United States Patent [19]

Lionetti et al.

[11] 4,018,911
[45] Apr. 19, 1977

[54] METHOD FOR LARGE VOLUME FREEZING AND THAWING OF PACKED ERYTHROCYTES

[75] Inventors: Fabian J. Lionetti, Milton; Stephen M. Hunt, Allston, both of Mass.

[73] Assignee: The United States of America as represented by the Secretary of the Navy, Washington, D.C.

[22] Filed: Nov. 10, 1975

[21] Appl. No.: 630,558

[52] U.S. Cl. .................................. 424/101; 62/69; 195/1.8
[51] Int. Cl.² .................. A61K 35/18; F25C 1/18; C12K 9/00
[58] Field of Search ................... 195/1.8; 424/101; 62/62, 64, 69

[56] References Cited

UNITED STATES PATENTS

| 3,758,382 | 9/1973 | Knorpp | 195/1.8 |
| 3,851,246 | 11/1974 | Curby et al. | 195/1.8 |
| 3,952,536 | 4/1976 | Faust et al. | 195/1.8 |

*Primary Examiner*—Sam Rosen
*Attorney, Agent, or Firm*—R. S. Sciascia; L. I. Shrago; C. E. Vautrain, Jr.

[57] ABSTRACT

A rigid metal holder having perforated side plates for containing plastic bags of human red blood cells for both freezing and thawing such cells is provided. Hydroxyethylstarch, HES, is used as the cryoprotective agent and, together with the perforated metal plates, permits the very fast freezing rates required to produce viable red cells. The HES is transfusable with the thawed cells so that post-thaw washing is obviated.

4 Claims, 6 Drawing Figures

METHOD FOR LARGE VOLUME FREEZING AND THAWING OF PACKED ERYTHROCYTES

The present invention concerns a method of and apparatus for freezing and thawing large volumes of erythrocytes and, more particularly, such a method and apparatus which are free of hazard to the recipients of the preserved red cells and avoid the present requirement that the thawed cells be washed prior to use.

It has long been attempted to prolong the period of viability of human red cells as much as possible so that the cells may be stored longer for emergency use or use in remote locations. The most promising procedure for preserving these human red cells or erythrocytes, that of freezing the cells in the presence of extracellular cryoprotectants, has been practiced for sometime. In such practice to the present time, suitable systems for full unit freezing containing transfusable extracellular cryoprotectants have not been devised which are free of hazard to the recipients of the preserved red cells. The arrival of hydroxyethylstarch, HES, as a red cell cryoprotectant has advanced the freezing-thawing process since it is both nontoxic and non-antigenic and thus need not be removed after thawing of the blood. HES in body circulation is slowly degraded by $\alpha$-amylases thereby entering the body pool of metabolizable carbohydrate and enhancing is acceptability clinically. In spite of its desirable features, the use of HES has to this time been confined to small volume units, i.e. 1–50 ml, due in part to the lack of suitable containers providing adequate heat exchange rates, and to the unavailability of adequate quantities of the starch.

Procedures have been developed for the elimination of cryoprotectants other than HES, such as glycerol, after thawing and the substitution of autologous plasma. It has been observed that the freezing and thawing rates with HES are much less critical in achieving high cell recoveries than polyvinylpyrollidone, PVP, a cryoprotectant unsuitable for clinical use. The present invention overcomes the failures in the prior art to achieve large volume or full unit cryopreservation using HES by providing a method of and means for freezing human erythrocytes in plastic bags, supported by rigid metal holders, in liquid nitrogen with 14% weight/volume of HES, and quickly thawing the erythrocytes upon removal from storage.

Accordingly, it is an object of the present invention to provide a method of and means for cyropreserving and protecting large volumes of human erythrocytes.

Another object of this invention is to provide a method of and means of freezing human erythrocytes which are free of hazard to the recipients of the preserved red cells.

A further object of this invention is to provide a method of and means for freezing human erythrocytes which employs a non-toxic and non-antigenic cryoprotectant and avoids the conventional step of washing the cells after thawing.

Other objects, advantages and novel features of the invention will become apparent from the following detailed description thereof when considered in conjunction with the accompanying drawings in which like numerals represent like parts throughout and wherein.

The present invention is basically a substantial improvement over an existing holder for thin flat plastic containers which is the subject of U.S. Pat. No. 3,776,411 issued Dec. 4, 1973 to James L. Luckadoo. Containers such as the Luckadoo container which are in use today substantially enclose the contents thereof in a casing made of a metal which is an excellent conductor of heat and/or cold depending on how the process is viewed. Applicants' holder includes substantial improvements and adds features to the Luckadoo container which are necessary to promote much improved heat and/or cold transfer and which may be stated generally as confining the material-containing bag to a much narrower thickness than that possible in known containers for bulk material, and allowing much greater freezing/thawing medium access through adding a multiplicity of apertures in the face plates of the container. Also, the face plates with the perforations themselves directly contact the bag throughout the major surface areas thereof and by such arrangement produce substantially more rapid freezing and thawing of the bag contents than was heretofore possible.

The present cryoholder thus is an important means for rapidly admitting a cooling or thawing medium to the interior of the holder wherein a preferably plastic bag containing human erythrocytes or other cells or liquids is securely held within a narrow space so that as great as possible a surface area is presented to the medium.

Figure 1:
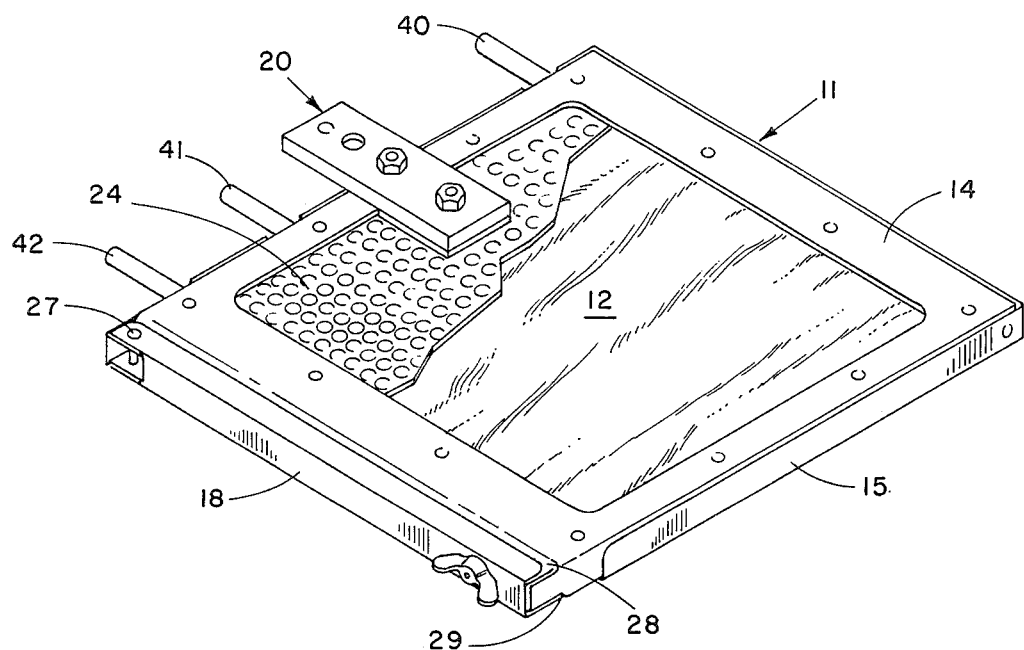
FIG. 1 is an isometric view of a preferred embodiment of the perforated metal cryoholder of the invention.
Figure 2:
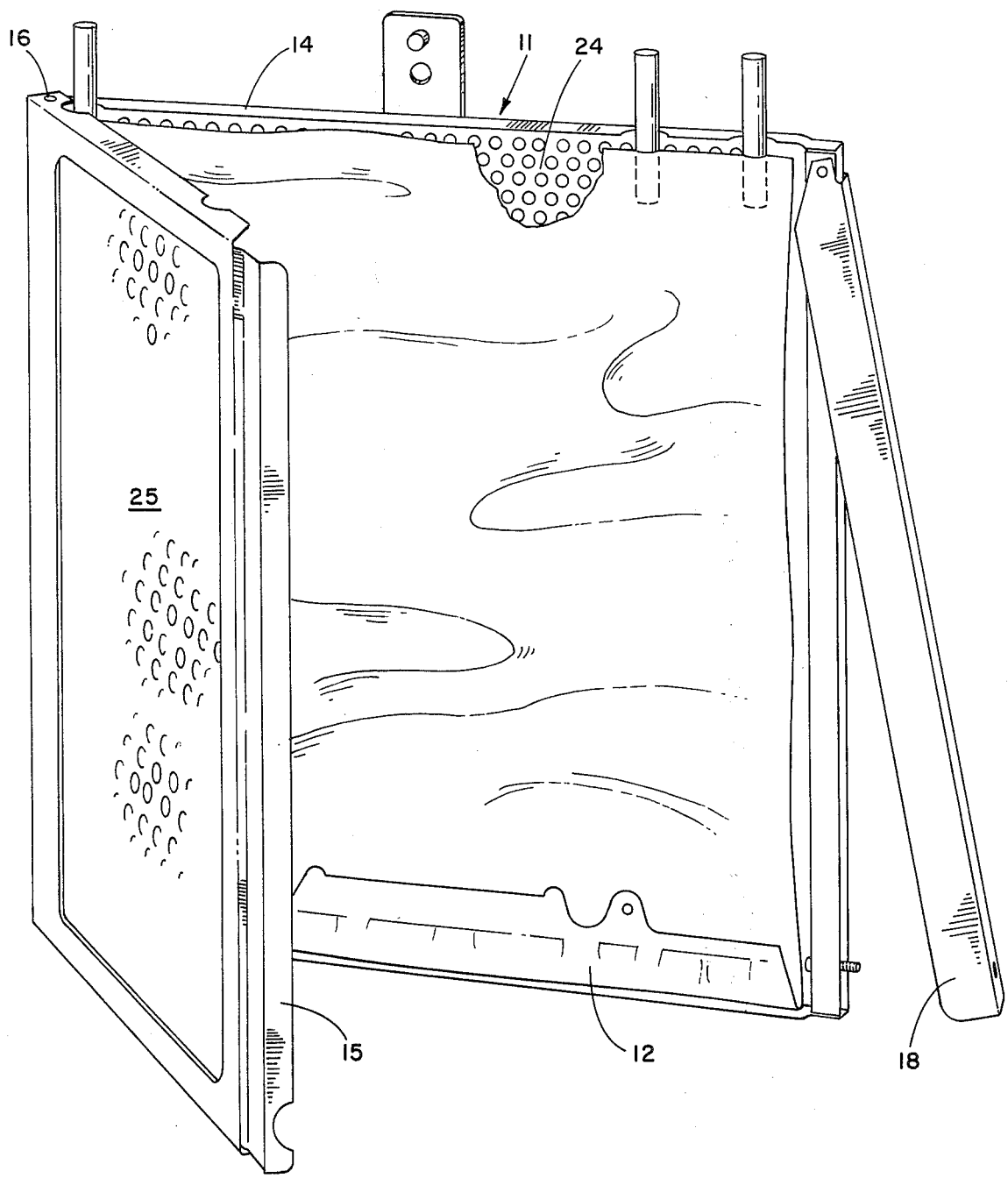
FIG. 2 is a perspective view of the embodiment of FIG. 1 opened to show the placement of a blood-freezing bag therein among other details.
Figure 3:
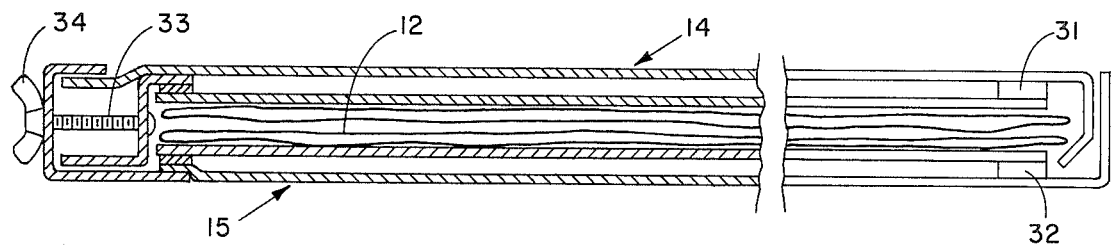
FIG. 3 is a sectional view of the embodiment of FIG. 1 taken along a line substantially corresponding to the line 3—3 therein.
Figure 4:
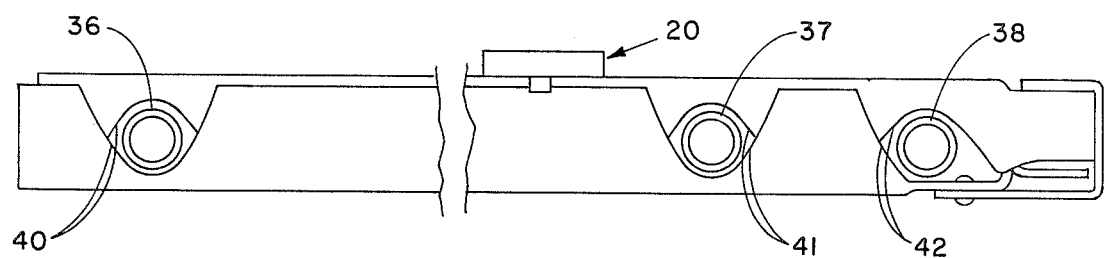
FIG. 4 is an end view of the embodiment of FIG. 1 showing the access ports for the blood-freezing and thawing bag tubes.
Figure 5:
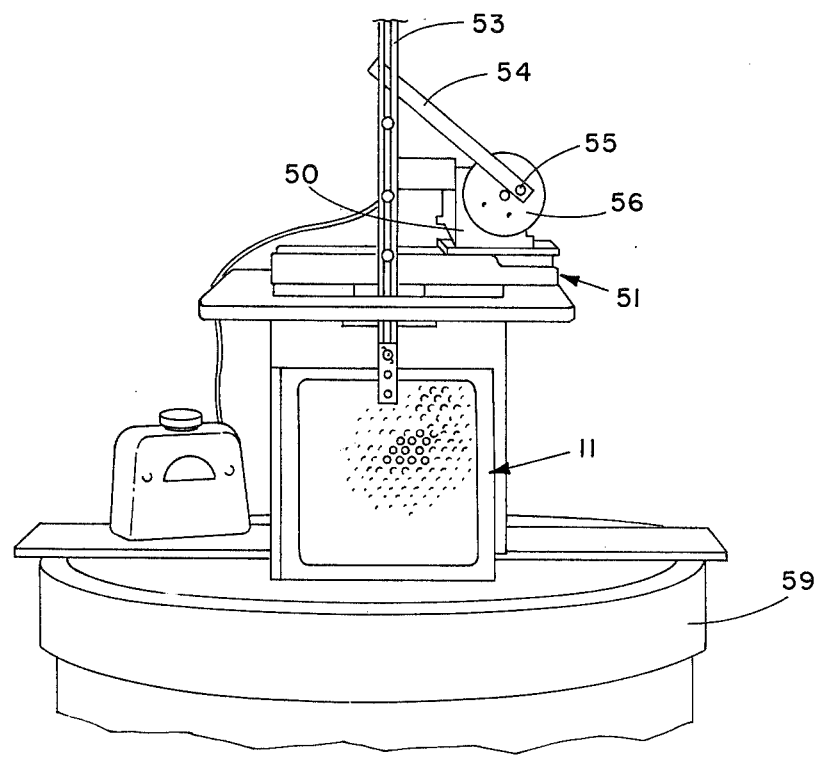
FIG. 5 is a perspective view of one form of apparatus for immersing a cryoholder into a bath of liquid nitrogen or other rapid freezing medium.

Referring to the drawings, FIGS. 1–4 illustrate an improved cryoholder 11 for shaping, confining, and immersing a bag 12 containing fluid or liquid material such as human red blood cells for rapid freezing and thawing, in assembled form in FIG. 1 and in more detail in FIGS. 2–4. As seen in FIG. 2, cryoholder 11 includes a pair of frame sections 14 and 15 which pivot about a common axis 16 and when snuggly fitted together are secured by a closure member 18 which is U-shaped and has extended sides that retain sections 14 and 15 along the entire length of the closure member. Cryoholder 11 is provided with a tab 20 for securing the device in a means for immersing the entire unit into a desired bath such as a pendulum shaker which is shown in FIG. 5. Cryoholder 11 is adapted to receive a plastic bag such as 12 and, as shown in FIGS. 3 and 4, to deploy the bag in a carefully controlled space. In FIG. 3 plastic bag 12 is shown in two layers due to it having been found preferable to fold the bag at its bottom edge to better contain and spread the substance to be frozen and/or thawed. Cryoholder 11 is provided with opposing perforated side panels 24 and 25 whose perforations are of a selected size and spacing so as to provide a maximum area for the medium to contact the bag while retaining the rigidity of frame necessary to maintain a substantially uniform cross section so as to promote freezing and thawing.

The cryoholder is essentially a flat tray having a close fitting cover and, in the embodiment shown, the tray member is section 14 while the cover member is section 15. Sections 14 and 15 preferably are made of aluminum or other non-corrosive metal while the perforated side panels preferably are made of a much more rigid material such as stainless steel so as to maintain a substantially constant cross section during vertical freezing with agitation of the contents of the bag when compressed between the opposing side panels. That is, to achieve the required very rapid rate of freezing in an attitude convenient for agitation, it is essential that the liquid to be frozen be maintained in a constant cross section of the device during the freezing process. For simplicity, closure member 18 is secured to and pivoted about a pin 27 in section 14 and both sections 14 and 15 are recessed as indicated at 28 and 29 a sufficient amount so that the side surfaces of closure member 18 are substantially planar and a continuation of the adjacent side surfaces of sections 14 and 15, as seen in FIG. 3. The desired spacing between perforated panels 24 and 25 is achieved by securing metal strips around the outer edges of the panels as indicated at 31 and 32 in FIG. 3. When sections 14 and 15 are folded together with bag 12 sandwiched therebetween, closure member 18 is passed over the ends of the sections and secured in place by a bolt 33 and a wing nut 34.

FIG. 4 is a top view of the cryoholder illustrating the location of a plurality of ports 36, 37 and 38 of bag 12 and the manner in which sections 14 and 15 are cut away as indicated at 40, 41 and 42 to permit passage of these ports. The three ports, which are tubes connected to and projecting from bag 12, are connections for filling the bag with a cell suspension and HES, admitting glucose fluid, etc. The ports may be used interchangeably for the foregoing purposes, however, to avoid contamination no port should be used for more than one purpose. In FIG. 3, the ports are not seen since the section is taken beyond their position. FIG. 4 is a view of the embodiment of FIG. 3 with the entire unit rotated 180° about an axis through the drawing sheet.

The various components of the cryoholder such as the frame sections, spacers and perforated plates, preferably are joined together by riveting. The perforations in panels 24 and 25 are necessary for optimum heat transfer and to prevent the insulation effect of gaseous nitrogen surrounding the unit as the liquid nitrogen boils on immersion in the liquid bath. The holes are limited in size in order to maintain a selected rigidity and it has been determined that desired freezing and thawing results are obtainable with 0.125 inches-diameter holes whose centers are spaced 0.200 inches apart and whose nearest adjacent perimeters are 0.100 inches apart. In other words, in a linear path along a line running through the center of one row of holes the spacing between adjacent holes would be substantially 0.300 inches while the spacing between the nearest holes in the transverse direction would be 0.100 inches. Such a spacing provided the preferred compromise between panel rigidity and access through the panel for the liquid nitrogen or other freezing medium. Such a spacing provides substantially 50% access through the surface for the freezing medium.

Cryoholder 11 is hinged and fitted with securing wing nut 34 to allow quick assembly before freezing and detaching after freezing from a shaking or vibrating apparatus such as that shown in FIG. 5. This apparatus includes a motor 50 which is secured to a platform 51 and connected to a vertical rod 53 by a rocker arm 54 which is connected off center from the rotation shaft of motor 50 by means of a bolt 55 passing through a hole in a flange 56. Cryoholder 11 is secured at the bottom of rod 53, rod 53 having a sufficient length to lower the cryoholder into a liquid nitrogen bath indicated at 59 which may be any commercially available unit. The following descriptions of materials and methods will provide an understanding of the success achieved in full unit freezing via the present invention in comparison with freezing of much smaller units through prior methods.

MATERIALS AND METHODS

Isolation of Red Cells

Units of whole blood, 450 ml, anticoagulated with CPD, 63 ml containing 206 mg citric acid, 1.66 g sodium citrate, 140 mg of sodium biphosphate and 1.6 g dextrose, were obtained from male donors at the Boston Red Cross Blood Center. They were centrifuged in the collection bags in an International PR-1 centrifuge for 3 min at 1000 g. The platelet rich plasma and the buffy coat plus 50 ml of topmost red cells were expressed and reserved for freezing separately.

Hydroxyethyl Starch

Hydroxyethylstarch, 40% w/v, McGraw Laboratories, Glendale, CA, Lot No. P1P005, degree of substitution 0.75, avMW 150,000 of 0.15 M NaCl was prepared by dissolving 42.7 g powder in 70 ml distilled water and adjusting volume to 100 ml. It was routinely made this way and used as a stock solution of 40% w/v.

The 25.0-ml Freezing Method

To 10 ml of plasma in a 50-ml plastic beaker was added 20 ml of 35% HES solution. The solution was well mixed and added slowly while mixing to 20 ml of packed red cells. The cell suspension was transferred to a 50-ml plastic syringe and 25 ml put into a Hemoflex bag, style 1000-2, made by Union Carbide Co., Films Packaging Division, Chicago, IL. Air bubbles were removed by rolling the bag on the edge of the counter top, allowing bubbles to leave via the puncture site. A loose-fitting glass plug was put into the open puncture site.

The small bag was then inserted into a larger Hemoflex bag, style 2480-2, by cutting off one end and making slits in the upper seam to pass the smaller bag through. These were then placed in a stainless steel "sandwich" holder not shown, and the open end of the larger bag folded three times and clamped to prevent entrance of liquid $N_2$. The holder was clamped to a pendulum shaker adjusted to oscillate at 160 cpm, and immersed, while shaking, into liquid nitrogen for 90 seconds. Bags and holder were completely immersed except for two protruding port tubes.

To thaw the blood, the holder was removed, the clamps taken off, the outer bag removed, and the inner bag with sample placed back in the holder. This was done quickly as possible, i.e. in 10–15 seconds. The holder with blood bag was suspended in a 47° C water bath shaking at 168 cpm for 30 seconds and the blood bag was removed from the holder. Thawed blood was cool to the touch, i.e. at approximately 180° C.

Full Unit Red Cells Freezing Method

Units, 405 ml each, of whole blood (CPD) were centrifuged in the plastic collection bags and platelet rich plasma and buffy coats removed as described above. The bags containing the packed red cells were weighed and the weight of an empty bag substracted. It was assumed that 1.0 ml of packed rbc equalled 1.0 g. The packed cells, 190–220 ml, were then transferred to a large Hemoflex bag, style 7450–3.

Plasma was centrifuged to remove platelets and 43–73 ml of platelet-free plasma added to 142 ml of HES, 40% w/v, with mixing in a satellite plastic bag. The final concentration of HES was 14% w/v. The plasma-HES solution was then forced into the freezing bag containing the packed cells and mixed by repeated inversion. Air bubbles were forced back into the pilot bag and the port to the freezing bag sealed. The cell suspension was then placed in cryoholder 11 attached to pendulum shaker 50-56 and immersed while shaking at 160 cpm in liquid nitrogen for 55–80 seconds. When stored, the blood was left in the holder and suspended in the liquid nitrogen in a Linde LR-40 cryorefrigerator.

The recovery was done by removing the the holder from the liquid and quickly immersing while shaking at 200 cpm for 65 seconds in a circulating water bath at 54° C.

The recovery of red cells after thawing was estimated from hemoglobin released into the plasma. The percentage of cells recovered was:

$$100 - [(\text{plasma Hb (g/ml)}/\text{total Hb (g/ml)}] \times (100 - \text{HCT})$$

The stability of the cells was estimated from the hemoglobin released when the thawed cell suspension was diluted 50 times with 0.15 M NaCl and incubated at 22° C for 30 min. Hemoglobin was measured as cyanmethemoglobin and $Na^+$ and $K^+$ in plasma by flame photometry. The ATP was determined in perchloric acid extracts with phosphoglycerate kinase, glyceraldehyde phosphate dehydrogenase and NADH, and 2,3 DPG in the same extracts as 3 PGA after treatment with 3 PGA mutase containing 2,3 DPG phosphatase in an endpoint method using phosphoglycollate.

Osmolality was determined by freezing point depression with a Precision Systems osmometer, and $pH$ with a Radiometer $pH$ meter with a capillary electrode.

Results

It is essential to maintain an adequate cross section during vertical freezing with agitation. For the 25.0-ml bag this was 1–2 mm and for the 405-ml bag this was 3 mm. The cryoholders used were hinged and fitted with a bolt to allow quick assembly and disattachment from the shaking apparatus. The holes in the side plates were found to be necessary for optimum heat transfer and to prevent the insulation effect of gaseous nitrogen surrounding the unit as the liquid nitrogen boiled on immersion of the unit. The best results were obtained when the assembled holder was dipped in a 40% solution of PVP in ethanol and dried prior to freezing. A summary of characteristics of cells frozen in liquid nitrogen by both methods is given in Table 1:

TABLE 1

CRYOPRESERVATION OF RED CELLS IN HES

Characteristics of Red Cells Frozen in 14% HES

| | | 25.0-ml method av ± SD $\eta = 10$ | Full-unit method (405ml) av ± SD $\eta = 10$ | |
|---|---|---|---|---|
| Cell yields Postthawed (%) | | 99.2 ± 0.3 | 97.2 ± 1.1 | |
| | Hours | | Hours | |
| Stability in 0.15 M NaCl (%) | 0.5 | 87.3 ± 3.9 | 0.5 | 75.7 ± 1.8 |
| | 1.0 | 85.9 ± 4.3 | 0.5 | 74.7 ± 1.5 |
| | 2.0 | 84.6 ± 4.4 | | after 24 hr at 4° C |
| | | $Na^+$ | $Na^+$ | $K^+$ |
| *Plasma cations (mequiv/liter) | Prefrozen | 135 ± 2.7 | 138 ± 7 | 0.81 ± 0.74 |
| | Postthawed | 118 ± 5.2 | 105 ± 8 | 32.4 ± 4.3 |
| | Change | −17 | −33 | +32 |
| ATP ($\mu$Moles/gHb) | Prefrozen | 3.4 ± 1.3 | | 4.9 ± 1.5 |
| | Postthawed | 2.6 ± 0.7 | | 4.7 ± 1.1 |
| | Change | −0.8 | | −0.2 |
| 2,3 DPG ($\mu$Moles/gHb) | Prefrozen | 18.3 ± 8.0 | | 9.3 ± 1.8 |
| | Postthawed | 18.7 ± 6.6 | | 8.3 ± 1.7 |
| | Change | +0.6 | | −1.0 |
| | | $K^+$ | | |
| *Plasma cations (mequiv/liter) | Prefrozen | 1.82 ± 0.54 | | |
| | Postthawed | 22.6 ± 3.50 | | |
| | Change | +21 | | |

The Table is organized to contrast properties of red cells frozen in the 25.0-ml volume system in the columns on the left and for the full freezing method on the right. For the 10 experiments detailed on the 25.0-ml method an average 99.2% of the cells were recovered in the postthawed state. When diluted, i.e. 1 ml cell suspension to 50 ml, with isotonic NaCl, these exhibited stability, as judged by hemoglobin release, ranging from 87.3± 3.9 to 84.5± 4.4% over a 2 hour interval at 22° C. During freezing and thawing, the cells gained 17 mequiv/liter of $Na^+$ from the supernatant and lost 21 mequiv/liter of $K^+$. For $Na^+$ this amounted to 13% of the plasma content. ATP decreased 23% while 2,3 DPG was unchanged. With respect to recovery of thawed cells, stability in saline after thawing, and $K^+$ loss by the cells, these results for comparable volumes frozen (25.0 ml) were similar to those recorded in the art.

Results obtained with full units are detailed in the right columns of Table 1. The characteristics are those of less stable postthawed red cells as 2% less cells were recovered and these exhibited greater osmotic instability. They also lost about twice the amount of cellular $K^+$ which exchanged for plasma $Na^+$. The ATP and 2,3 DPG values showed minor and possibly insignificant losses. The relatively low magnitude of 2,3 DPG is unexplained and may reflect storage loss due to accidental slight acidification of perchloric acid extracts stored in the frozen state for several weeks prior to analysis. Despite the relatively low stability in saline no further deterioration occurred over 24 hours of refrigerated storage of thawed cells.

Experience with large volume freezing with the present bag and holder has indicated progressive increases in red cell yield and stability as the efficiency of heat transfer from the blood has been improved as manifested by faster times to freeze the units. In the five most recent experiments the bag and holder wire immersed briefly in a suspension of PVP in ethanol to reduce the size of nitrogen gas bubbles on immersion of the units in liquid nitrogen. This produced the best results yet obtained as the highest yields of cells were observed, $98.2 \pm 0.3$, and cell stability in isotonic NaCl for 0.5 hours was 79.5. These units froze in 60 seconds and averaged 10 seconds faster freezing than the Units reported in Table 1.

Figure 6:
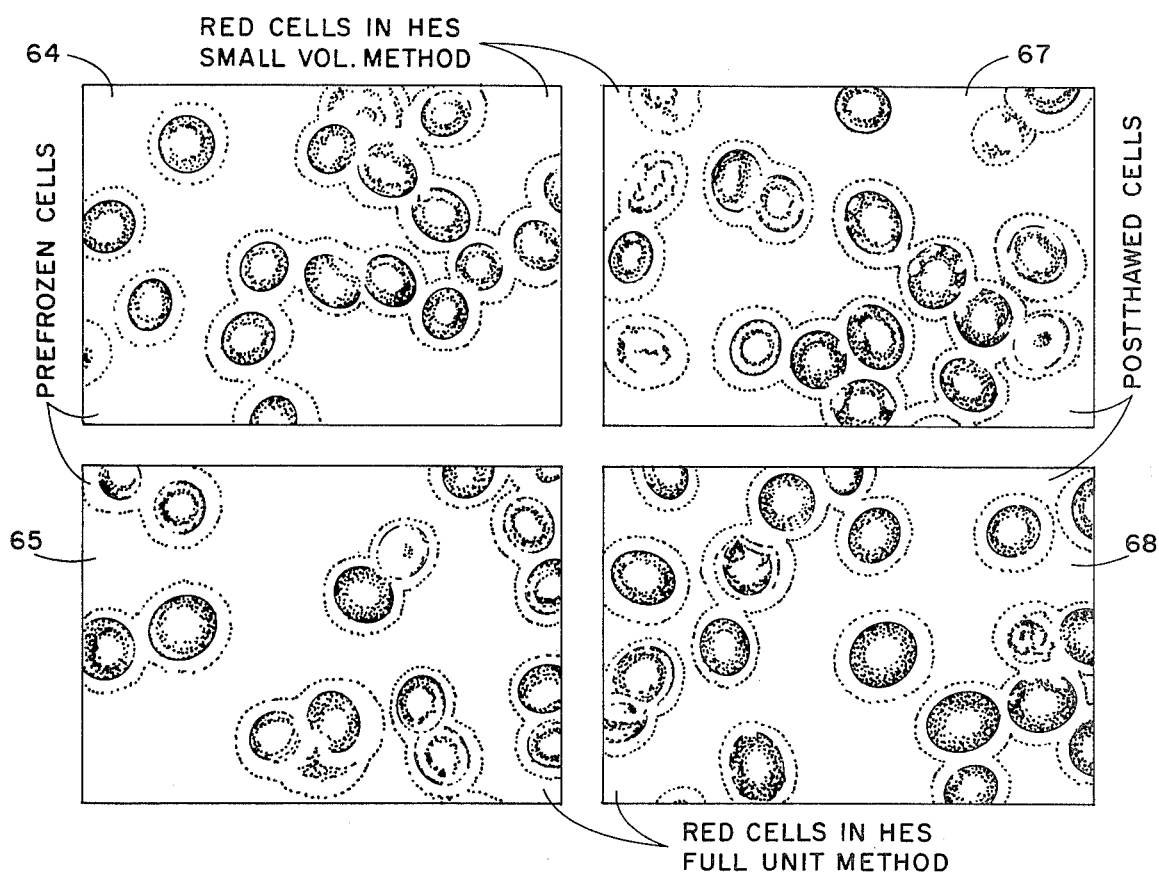
FIG. 6 is a comparison of magnified cells in their condition just before freezing and immediately after thawing in accordance with the process of the present invention.

Morphological examination of red cell suspensions in HES and plasma just before freezing and immediately after thawing revealed similar characteristics as shown in FIG. 6. This figure illustrates red cells in 14% HES with the cells fixed in glutaraldehyde, 0.5%, photographed to stress phase contrasts, and magnified 800X. the prefrozen samples by either the small or large volume methods, panels 64 and 65, gave typical morphology of normal red cell suspensions, while the thawed samples, panels 67 and 68, showed a moderate number of crenated discs and echinocytic forms. Panels 64 and 67 are photographs of cells frozen via the small volume method while panels 65 and 68 are of cells frozen by the full unit method. The magnitude of crenated discs and echinocytic forms resulting from both methods of freezing was approximately the same.

By means of the small volume method it was determined the whole blood (CPD) could be stored at 4° C up to one week prior to freezing and thawing with no storage produced cell changes as shown in Table 2 hereinafter presented. Two units of whole blood were sampled four times each during a 7-day interval at 4° C. Data for Day 1 was taken from 10 different units. Mixtures were frozen with 14% HES, thawed immediately and tested. Cell recovery and stability in 0.15 M NaCl were essentially the same over the interval. The ATP and 2,3 DPG showed no progressive loss although variability in ATP and 2,3 DPG can be attributed to analytical variation due to preparation of the extracts. The $Na^+$ and $K^+$ were exchanged between cells and plasma and were of similar magnitude for each period tested.

TABLE 2

Effects of Prefreeze Storage at 4° C on Red Cells Frozen in HES

Small Volume Method

| Storage time at 4° C before freezing (days) | Cell Yield Postthawed (%) | Stability in 0.15 M NaCl for 0.5 Hr. (%) |
|---|---|---|
| 1 ($\eta = 10$) | 99.1 ± 0.3 | 83.2 ± 5.3 |
| 2 ($\eta = 2$) | 99.6 | 88.5 |
| 4 ($\eta = 2$) | 99.4 | 88.9 |
| 7 ($\eta = 2$) | 99.3 | 86.0 |

| Storage time at 4° C before freezing (days) | Changes | | | |
|---|---|---|---|---|
| | ATP | 2,3 DPG | $Na^+$ | $K^+$ |
| | ($\mu$Moles/g Hb) | | (mequiv/liter plasma) | |
| 1 ($\eta = 10$) | −0.6 ± 0.4 | −0.3 ± 0.2 | −24 ± 4 | +24 ± 1 |
| 2 ($\eta = 2$) | −1.2 | −1.4 | −27 | −20 |
| 4 ($\eta = 2$) | +0.3 | −1.2 | −22 | +19 |
| 7 ($\eta = 2$) | +0.02 | −0.2 | −13 | +15 |

Frozen Red Cells Stored for 24 Hr $\eta = 1$

| Temperature of Storage | Cell Yield Postthawed (%) | Stability in 0.15 M NaCl for 0.5 Hr. (%) |
|---|---|---|
| 4° C | 98.9 | 79.4 |
| −196° C | 98.7 | 78.6 |

| Temperature of Storage | Changes | | | |
|---|---|---|---|---|
| | ATP | 2,3 DPG | $Na^+$ | $K^+$ |
| | ($\mu$Moles/g Hb) | | (mequiv/liter plasma) | |
| 4° C | +0.3 | −0.2 | −24 | +27 |
| −196° C | +0.5 | −0.6 | −23 | +27 |

Differences observed between Days 2, 3, 4 and 7 are probably due to variations in freezing or thawing rates. An experiment comparing red cells frozen in liquid nitrogen, immediately thawed and stored at 4° C for 24 hours with a similar freezing where cells were maintained in liquid nitrogen for 24 hours prior to thawing showed no difference, Table 2, bottom. This suggests that postthawed cells remain stable at least 24 hours at 4° C as was also observed with the full unit method, Table 1.

In the large-volume method using all the packed red cells in a unit after removal of platelet rich plasma and buffy coat, a single bag was sandwiched between large perforated aluminum plates. The results of eight recent freezings and short-term storage in liquid nitrogen vapor gave cell recoveries of 97.2 ± 1.1%, and stabilities in saline of 75.7 ± 1.8%. Relatively small losses of ATP and 2,3 DPG were observed. The cells gained 33 mequiv of $Na^+$ and lost 31 mequiv of $K^+$. Assuming acceptable 24 hour posttransfusion survival can be achieved, the feasibility of freezing full units of red cells in a one-step procedure has been demonstrated.

In another embodiment of the process of the invention fourteen full units of packed cells, i.e. plasma and 40% HES at 142 ml, were mixed in the same manner and proportion as described supra to obtain a final HES concentration of 14%. The volume of packed cells and plasma was maintained at 263 ml, with the volume of packed cells varying between 190 and 220 ml. In some of the units prepared, packed cells were washed three times with equal volumes of 0.15 NaCl. In freezing experiments with these cells, 0.15 NaCl was substituted for plasma. The cell suspensions in the style 7450-3 Hemoflex bags, discussed supra, were then chilled at substantially 4° C for substantially 45 minutes, removed and placed in a cryoholder that had been prechilled to 0° C. The units were then frozen by immersion in liquid nitrogen and stored as described infra. In this embodiment, the cryoholders were suspended in liquid nitrogen up to the bag ports while being held stationary until bubbling stopped, i.e. for about 55 to 60 seconds. The units were then stored by lifting their cryoholders into the vapor above the liquid nitrogen.

Thawing of the units in this embodiment was accomplished either by removing the cryoholder from the nitrogen vapor and immersing while attached to the pendulum shaker in a water bath at substantially 54° C while shaking at 200 cpm for substantially 60 seconds, or by placing the units in the basket of a shaking water bath at 200 cpm and at substantially 54° C with the water stirred continuously preferably by a pump. After thawing, an equal volume of 6% glucose was admixed to the thawed units in the Hemoflex bags. The units were then centrifuged in a refrigerated centrifuge for 30 minutes at 2500 g and the supernatant was expressed.

The results of a study of 10 units of this embodiment show all yields to be 98.4 ± 0.5% as thawed, and 98.0 ± 0.5% when resuspended in glucose of 3% final concentration. A significant improvement to 87.8% of thawed cells stable to an osmotic stress by dilution at 1:50 with 0.15 NaCl was achieved. Noted in assessing cellular changes during freezing and thawing of these units was a relatively large loss of cellular K when exchanged for $Na^+$ of the medium of approximately the same magnitude. Along with postthawed cellular recoveries and cellular stability to a large dilution, the changes in $Na^+$ and $K^+$ in the medium were the most useful indicators of freezing and thawing efficiency. With this system embodiment, substantially 30 mequiv of $K^+$ was lost by the cells and an equivalent amount of $Na^+$ was incorporated.

The oxygen function of the red cells of this embodiment frozen in 14% HES was studied over a period of 6 months of storage in liquid nitrogen vapor. The units were collected, processed, frozen and stored over a three-week interval. At selected times the bags were thawed and elevated in groups of two or three units. Results indicate that storage up to 6 months did not affect yield or stability of the thawed cells.

The stability and other values of the full-unit method thus may improved by raising the water path temperature from 47° C to 54° C, increasing the shaking to 200 cpm, and lengthening the thawing time to 65 to 70 seconds. Units thawed in this manner contained no residual ice and were warm to touch. Oxygen function, determined as oxygen pressure in millimeters required to saturate 50% of the cellular hemoglobin, was in the normal range throughout the storage interval of six months. It was unaffected by the presence of starch in the thawed sample and slightly less when resuspended in 3% glucose. Over a 24-week period the $Na^+$ and $K^+$ exchange was similar for all units, suggesting that this effect is directly related to freezing and thawing of the blood.

There is thus provided a method of and apparatus for freezing packed erythrocytes in units exceeding 400 ml in volume with 14% w/v HES. The units are deployed preferably in a plastic bag which is confined to a flat shape substantially 3 mm thick and immersed with or without agitation for from about 55 to about 85 seconds in a quick-freezing bath preferably of liquid nitrogen. Recovery by thawing is accomplished by removing the bag holder and bag from storage and quickly immersing while shaking at substantially 200 cpm for from 65-90 seconds in a water bath maintained at from 47°-54° C. Recovery also may be accomplished by placing the bag and holder in a shaking or vibrating water bath at a temperature of substantially 54° C with the water stirred continuously by a pump or other means.

Small-volume units, which are much more effectively frozen and thawed, were used as a reference and the results of the full-unit method compared very favorably therewith. Optimum results derived from the small-volume method averaged about 99.2% cell recovery with stability as determined by hemoglobin release ranging from 87.3 ± 3.9% to 84.5 ± 4.4% over a 2-hour interval at 22° C. Results from one embodiment of the full-unit method were a cell yield of 98.2 ± 0.3% and a cell stability in isotonic NaCl for 0.5 hours of substantially 79.5%. A second embodiment of the full-unit method gave a cell yield of 98.4 ± 0.5% and a stability of substantially 87.8%.

The cryoholder may be made of a variety of metals or alloys suitable for the rapid changes of temperature required. Aluminum plates outperformed perforated carbon steel plates and are preferred thereover. A selected combination of number of holes, sizes of holes, spacing of holes, plate thickness and interval cross section for obtaining maximum results was determined. The values giving best results were a hole size of 0.125 ± 0.031 inches and a plates thickness of 0.065 ± 0.031 inches with rows of holes staggered 0.2 inches on centers and offset 0.1 inches.

Obviously many modifications and variations of the present invention are possible in the light of the above teachings. For example, a sandwich form of perforated aluminum plates held together with clips could be used, the shape of the perforations could be other than circular to permit varied spacing within a minimum total exposed area, and other means for agitating the baths and/or the cryoholder could be employed.

What is claimed is:

1. A method of freezing and thawing large volumes on the order of 400 ml or more of human red blood cells which thereafter may be transferred without hazard to the recipient comprising:

centrifuging a selected volume of whole blood to separate platelets and buffy coats;

removing platelets rich plasma and buffy coats by forcing topmost fluid and cell layers under pressure out of the blood container;

transferring the remaining cells to a freezing bag susceptible of being spread substantially flat to a desired area and spacing of the major surfaces;

adding hydroxyethyl starch to the platelet-free plasma in a proportion substantially of 142 ml of hydroxyethyl starch, 40% weight/volume, plus 263 ml of packed cells plus plasma;

mixing the hydroxyethyl starch and the plasma in a satellite container;

forcing the hydroxyethyl starch-plasma solution into the freezing bag containing the packed cells and mixing the constituents by repeated inversion;

forcing air bubbles back into the satellite bag and sealing the freezing bag; and placing the bag in a cryoholder adapted for rapid heat transfer and immersing the cryoholder in a liquid nitrogen bath for an interval on the order of from 1 to 1⅓ minutes while shaking at a rate of substantially 160 cpm.

2. The method of claim 1 and further including recovering matter by rapid thawing by immersing the cryoholder in a water bath at substantially 47° C while shaking at the same rate for substantially 1 minute.

3. The method of claim 1 and further including recovering the frozen matter by rapid thawing by immersing the cryoholder in a water bath at substantially 54° while shaking at a rate of substantially 200 cpm for substantially 1 minute.

4. The method of claim 3 and further including admitting 6% glucose after thawing to stabilize the red cells and reduce the viscosity of the cell suspensions and thereafter removing excess glucose and fluid to remove excess hydroxyethyl starch and concentrate the red cells.

* * * * *